(12) United States Patent
Morales et al.

(10) Patent No.: US 6,335,533 B1
(45) Date of Patent: Jan. 1, 2002

(54) ELECTRON MICROSCOPY SAMPLE HAVING SILICON NITRIDE PASSIVATION LAYER

(75) Inventors: Guarionex Morales, Santa Clara; Dawn Hopper, San Jose; Lu You, Santa Clara, all of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/206,674

(22) Filed: Dec. 7, 1998

(51) Int. Cl.[7] .................................. H01J 37/00
(52) U.S. Cl. ..................................... 250/492.2
(58) Field of Search ..................... 250/492.3, 492.2, 250/310, 311

(56) References Cited

U.S. PATENT DOCUMENTS

| | | | |
|---|---|---|---|
| 3,879,840 A | * 4/1975 | Ames et al. | 29/589 |
| 4,980,307 A | 12/1990 | Ito et al. | 437/40 |
| 5,010,024 A | 4/1991 | Allen et al. | 437/24 |
| 5,483,097 A | 1/1996 | Ohtsuki et al. | 257/632 |
| 5,607,566 A | * 3/1997 | Brown et al. | 204/418 |
| 5,620,909 A | 4/1997 | Lin et al. | 438/703 |
| 5,633,202 A | 5/1997 | Brigham et al. | 438/763 |
| 5,952,658 A | * 9/1999 | Shimase et al. | 250/309 |
| 6,144,097 A | * 11/2000 | Asahina et al. | 257/751 |

* cited by examiner

*Primary Examiner*—Kiet T. Nguyen
(74) *Attorney, Agent, or Firm*—Foley & Lardner

(57) ABSTRACT

A transmission electron microscopy (TEM) or scanning electron microscopy (SEM) sample preparation method includes the steps of depositing a metal layer on top of a substrate, depositing a silicon nitride passivation layer on top of the metal layer, and cutting the substrate and the metal and passivation layers to expose their cross-sections for examination by electron microscopy. As a result, a TEM/SEM sample having sharp, well-defined boundaries is produced.

17 Claims, 4 Drawing Sheets

US 6,335,533 B1

ELECTRON MICROSCOPY SAMPLE HAVING SILICON NITRIDE PASSIVATION LAYER

BACKGROUND OF THE INVENTION

1. Field of the Invention

The invention relates generally to electron microscopy and, more particularly, to an electron microscopy image sample having a silicon nitride ($Si_3N_4$) passivation layer.

2. Description of the Related Art

Electron microscopy has been used to image semiconductor device cross-sections so that process characteristics, such as deposition rates, thicknesses, interfaces, via or step coverage, and other particular features, can be studied.

Either transmission electron microscopy (TEM) or scanning electron microscopy (SEM) has been used. TEM provides better resolution than SEM and its use has become more common as semiconductor device dimensions have become smaller. TEM is especially useful to study thin film process characteristics. However, TEM sample preparation is more complicated than SEM sample preparation.

In the conventional electron microscopy sample preparation, a spin-on-glass (SOG) layer is disposed on top of the semiconductor device being studied. Generally, the semiconductor device being studied includes at least a metal layer as the top layer and a silicon base. The SOG layer protects the metal layer from mechanical damage and functions to hold all of the layers together during the subsequent cutting process. The cutting process is necessary so that the cross-section of the sample can be exposed for imaging by the electron microscope.

Conventionally, the SOG layer is disposed on top of the study sample in the following manner. First, SOG is liquefied using a solvent. Second, the liquid SOG is dripped on top of the sample. Third, the sample is spun, forcing the liquid SOG to disperse evenly on top of the sample. Fourth, the liquid SOG is cured at temperatures above 400° C. to remove the solvent from the SOG. At this curing stage, the SOG is subject to high enough temperatures (>400° C.) where it reacts with part or all of the underlying metal layer to produce low quality TEM/SEM samples.

SUMMARY OF THE INVENTION

An object of this invention is to provide a method for preparing an improved sample for examination using either TEM or SEM.

The sample preparation method according to the present invention includes the steps of depositing a metal layer on top of a substrate, depositing a passivation layer comprising silicon and nitrogen on top of the metal layer, and cutting the substrate and the metal and passivation layers to expose their cross-sections for examination by electron microscopy.

The above method produces a TEM/SEM sample having sharp, well-defined boundaries. Consequently, it facilitates the study of process characteristics, including deposition rates, thicknesses, metal-substrate interface, and via or trench sidewall and bottom coverage. The method according to the present invention is especially effective when studying process characteristics of thin and very thin metal films.

Another object of the invention is to provide an electron microscopy image sample having sharp, well-defined boundaries. The sample according to the invention includes a substrate, a metal layer disposed on top of the substrate, and a passivation layer comprising silicon and nitrogen disposed on top of the metal layer, and has its cross-section cut for imaging by either transmission or scanning electron microscopy.

In the invention, the substrate underlying the metal layer may be a semiconductor base, a superconductor base, or any other base on top of which thin metal films are deposited. The semiconductor base may be, for example, a silicon base or a silicon base having one or more layers, e.g., $SiO_2$, $Si_3N_4$, or polysilicon layer, disposed on top of the silicon base. The superconductor base may be, for example, tantalum aluminide ($TaAl_2O_3$).

The metal layer comprises one of the following layers: titanium (Ti), titanium nitride (TiN), tantalum (Ta), tantalum nitride (TaN), aluminum (Al), copper (Cu), tungsten (W), tungsten nitride ($WN_x$), and other layers conventionally used as metal layers in semiconductor process technology including other barrier-metal layers. A metal layer is considered to be "thin" when it is less than about 1000 angstroms. A metal layer is considered to be "very thin" when it is less than about 100 angstroms.

The passivation layer comprises silicon nitride. A TEM/SEM sample employing silicon nitride layer as the passivation layer has sharp, well-defined boundaries because the silicon nitride layer is less prone to react with the underlying metal layer than a SOG layer, especially when the silicon nitride layer is deposited at temperatures less than 400° C.

Preferably, the silicon nitride layer is deposited at low temperatures, between 300 and 350° C., to minimize any reactions between the silicon nitride layer and the underlying metal layer. To carry out the low temperature deposition, plasma-enhanced chemical vapor deposition (PECVD) is employed.

Additional objects, features and advantages of the invention will be set forth in the description of preferred embodiments which follows.

BRIEF DESCRIPTION OF THE DRAWINGS

The invention is described in detail herein with reference to the drawings in which.

The accompanying drawings, which are incorporated in and constitute a part of the specification, illustrate presently preferred exemplary embodiments of the invention, and, together with the general description given above and the detailed description of the preferred embodiments given below, serve to explain the principles of the invention.

DETAILED DESCRIPTION OF THE PREFERRED EMBODIMENT

Figure 1:
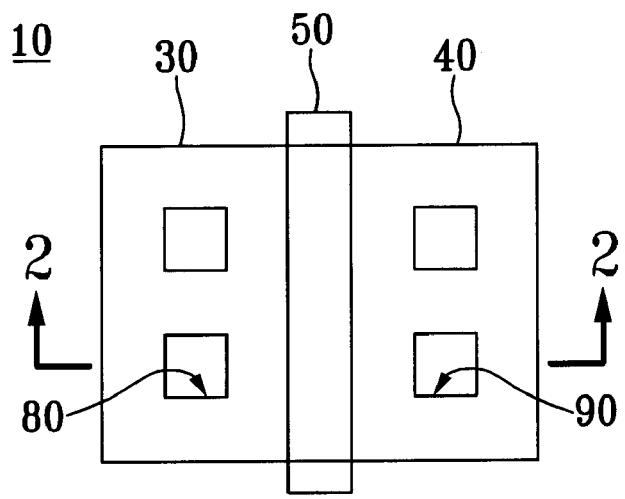
FIG. 1 is a plan view of a semiconductor device.

The invention is illustrated using a semiconductor device 10. FIG. 1 shows a plan view of the semiconductor device 10 and FIG. 2 shows the cross-sectional view of the semiconductor device 10 taken along line 2—2 of FIG. 1.

The semiconductor device 10 includes a silicon base 20, two active regions in the silicon base 20 formed by adding dopants, namely a source region 30 and a drain region 40, and a polysilicon gate 50. A gate oxide layer 60, which is typically silicon oxide ($SiO_2$), is provided between the gate 50 and the silicon substrate 20. An insulator layer 70, which may be, for example, another $SiO_2$ layer or a $Si_3N_4$ layer, covers the gate 50 and the gate oxide layer 60. The insulator layer 70 is deposited onto the gate 50 and the gate oxide layer 60 by chemical vapor deposition (CVD). Etching is carried out to form openings 80 and 90 in the gate oxide layer 60 and the insulator layer 70.

Figure 2:
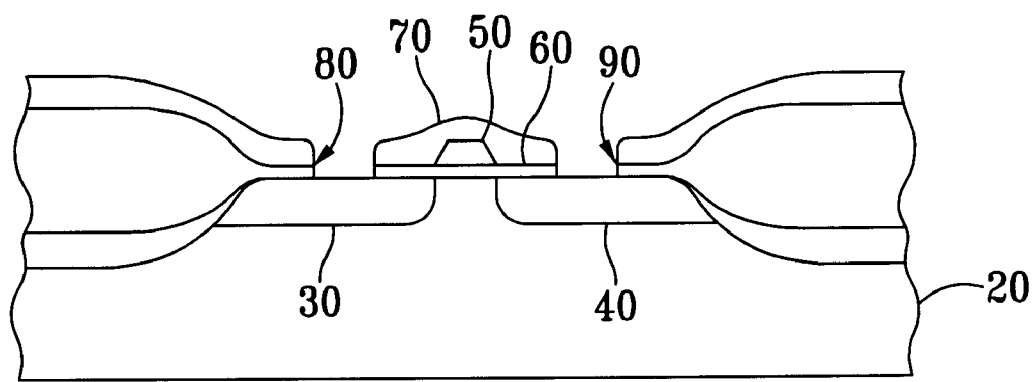
FIG. 2 is a cross-section of the semiconductor device of FIG. 1.

In the description that follows, the semiconductor device 10 illustrated in FIGS. 1 and 2 will be referred to as a "substrate." In alternative embodiments of the invention, this "substrate" may include only the silicon base 20, or a $SiO_2$ or $Si_3N_4$ layer in addition to the silicon base 20. In this regard, the term "substrate" is being used to generally define the elements or layers that underlie a layer of metal film. As noted earlier, the "substrate" may be a superconductor base or any other base on top of which a thin metal film is deposited.

FIGS. 3A to 3E illustrate the method according to the invention.

Figure 3A:
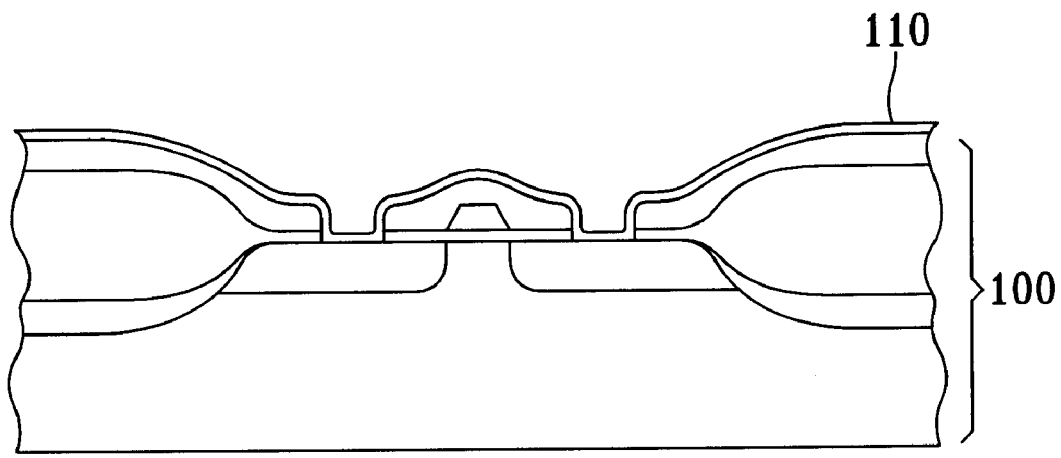
FIGS. 3A to 3E illustrate the electron microscopy sample preparation method according to the invention.

First, a metal layer 110 is deposited on top of the substrate 100 to a thickness of about 100–1000 angstroms. The invention is illustrated here with a metal layer having a thickness of about 100–1000 angstroms but is applicable to other thickness ranges of the metal layer, e.g., 10–100 angstroms, 50–100 angstroms, 100–200 angstroms, etc. The resulting structure is illustrated in FIG. 3A. Any conventional method for depositing metal may be used. The metal layer 110 comprises one of the following layers: Ti, TiN, Ta, TaN, Al, Cu, W, $WN_x$ and other metal layers conventionally used in semiconductor process technology, including other barrier-metal layers.

Figure 3B:
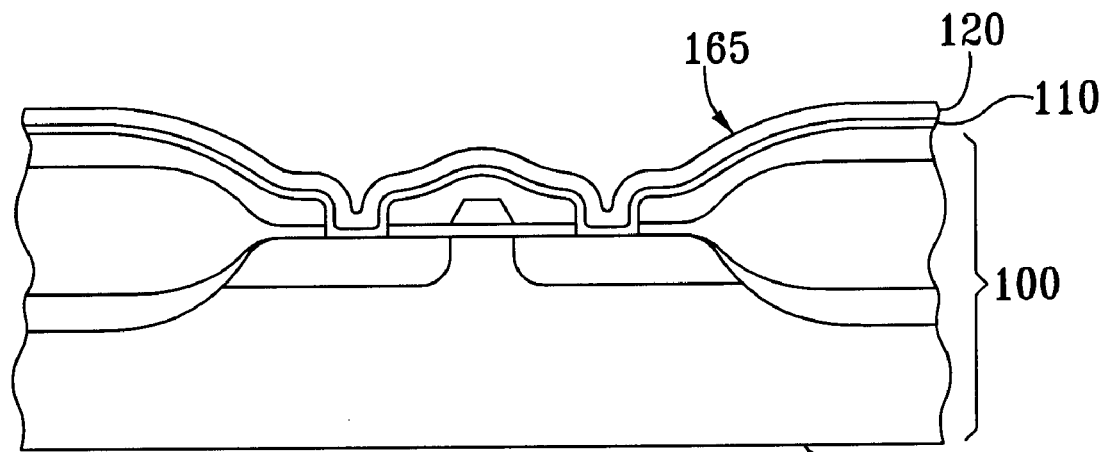

Second, a $Si_3N_4$ layer 120 is deposited on top of the metal layer 10. The resulting structure is illustrated in FIG. 3B. PECVD is employed and the deposition temperature is kept less than 400° C., preferably between 300° C. and 350° C. Other methods of depositing $Si_3N_4$ may be employed so long as the deposition temperature is kept at similar low temperatures. Alternative to a $Si_3N_4$ layer, a silicon oxynitride layer may be employed, so long as its deposition temperature is kept below the temperature where the silicon oxynitride layer is likely to react with the underlying metal film.

Figure 3C:
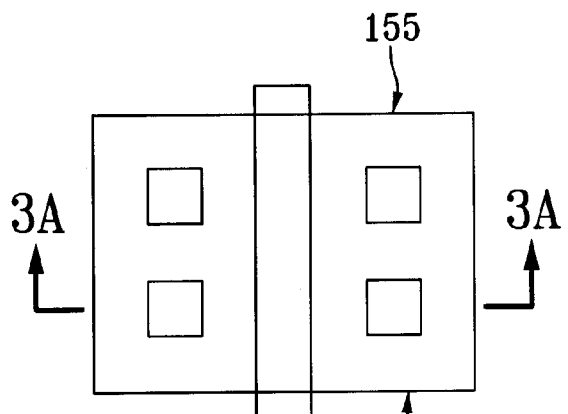

Third, the structure of FIG. 3C (FIG. 3C is a plan view of FIG. 3B) is cut along cross-section line A—A so that a cross-section of the SEM/TEM sample, like the one shown in FIG. 3B, is exposed for imaging. The cutting is performed by employing methods that are known in the art.

Figure 3D:
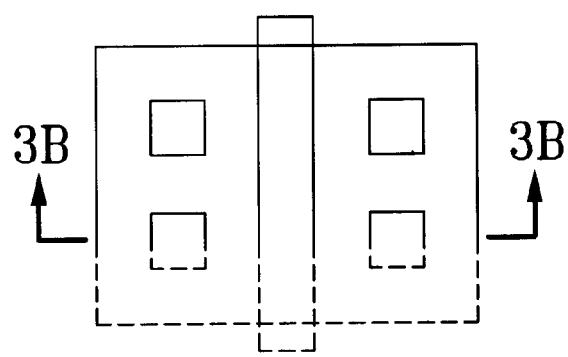
Figure 3E:
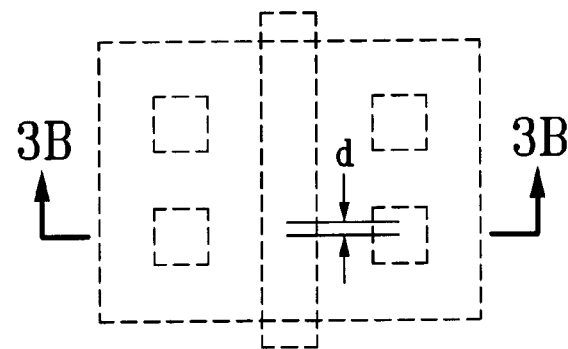

For example, the device illustrated in FIG. 3C may be cut along line A—A by a method known as cleave and polish. The resulting structure is illustrated in FIG. 3D for an SEM sample and in FIG. 3E for a TEM sample. (The cut portions of the device are illustrated in broken lines and the remaining portions of the device are illustrated in solid lines.) To obtain the SEM sample, polishing is carried out on only one side (i.e., the lower side 150 as illustrated in FIG. 3C) of the device. To obtain the TEM sample, polishing is carried out on both sides of the device (i.e., the lower side 150 and the upper side 155 as illustrated in FIG. 3C). A very thin strip (e.g., depth "d" of the metal layer in the imaging direction B—B is about 50–100 angstroms) is required for TEM imaging because the electrons must be able to penetrate (i.e., transmitted through) the TEM sample. Polishing may be performed by mechanical abrasions or ion milling.

Alternatively, the device illustrated in FIG. 3C may be "dimpled." This process includes the steps of: (1) polishing from the bottom surface 160 (see FIG. 3B) to the top surface 165 (see FIG. 3B) so that only about 99% of its thickness remains and the device becomes transparent from the top; (2) polishing one of the sides (either the lower side 150 or the upper side 155 of the device); and (3) ion milling a bowl on the top of the device. This final step is not necessary to prepare the SEM sample. It is necessary for the TEM sample because it cuts out a bowl on the top surface 155 of the device illustrated in FIG. 3D so that a thin wall is formed along line B—B. The thin wall has a thickness of about 50–100 angstroms so that TEM imaging may be performed.

Figure 4:
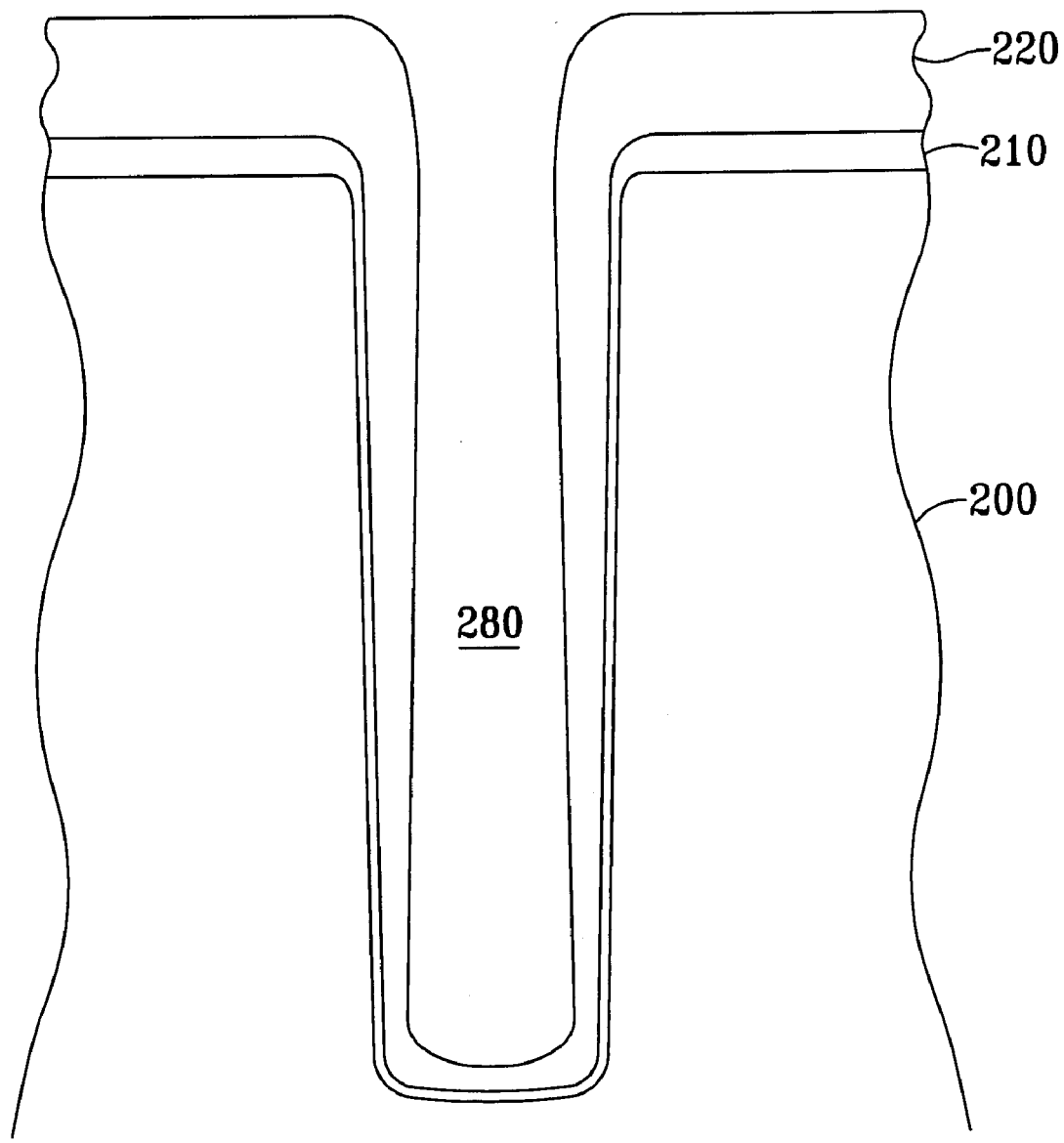
FIG. 4 illustrates a cross-section of an electron microscopy sample produced using the method according to the invention.

FIG. 4 illustrates a cross-section of another electron microscopy sample produced in the above-described manner. This sample has a high aspect ratio (hole height/width >3) contact hole 280. Because of the high aspect ratio, the sidewall and bottom coverage of the metal layer within the contact hole 280 is poor. Typically, for a high aspect ratio contact hole, the sidewall coverage is less than 10% of the metal layer thickness at the top of the contact hole and the bottom coverage is about 12% of the metal layer thickness at the top of the contact hole.

The sample further includes a substrate 200. A metal layer 210 having a thickness of about 100–1000 angstroms is disposed on top of the substrate 200. The metal layer 210 comprises one of the following layers: Ti, TiN, Ta, TaN, Al, Cu, W, $WN_x$, and other metal layers conventionally used in semiconductor process technology, including other barrier-metal layers. The top layer in FIG. 4 is a silicon nitride layer 220 having a thickness of about 2000–3000 angstroms. The silicon nitride layer 220 functions as the passivation layer.

The invention is particularly useful in imaging a sample having a high aspect ratio contact hole as in FIG. 4, because the silicon nitride layer 220, unlike an SOG layer, suppresses reactions with the underlying metal layer. As a result, with the invention, the small amount of metal layer remaining on the sidewalls and the bottom of the contact hole retain their thicknesses to permit higher quality imaging of the metal layer by electron microscopy.

When the sample of FIG. 4 is used for TEM imaging, the unfilled portion of the contact hole 280 is filled in with an SOG layer (not shown). This SOG layer is isolated from the metal layer 210 by the passivation layer 220 and thus does not react with the metal layer as in conventional samples. As a result, the SOG layer provides the sample with an additional protective layer while maintaining the quality of the resulting TEM sample.

While particular embodiments according to the invention have been illustrated and described above, it will be clear that the invention can take a variety of forms and embodiments within the scope of the appended claims.

We claim:

1. A method of obtaining an image of an interface between a metal layer and a substrate, comprising the steps of:
    depositing the metal layer on top of the substrate;
    depositing a passivation layer over the entire top metal layer, said passivation layer being an uppermost layer and comprising silicon and nitrogen;
    cutting the substrate and the metal and passivation layers to expose their cross-sections; and
    imaging the cross-sections through an electron microscope.

2. The method according to claim 1, wherein the step of imaging includes the step of imaging through a transmission electron microscope.

3. The method according to claim 1, wherein the step of imaging includes the step of imaging through a scanning electron microscope.

4. The method according to claim 1, further comprising the step of disposing an SOG layer on top of the passivation layer before the step of cutting so that said SOG layer becomes the uppermost layer instead of said passivation layer.

5. The method according to claim 1, wherein the step of depositing includes the step of depositing a silicon nitride layer at temperatures between 300° C. and 350° C.

6. The method according to claim 5, wherein the silicon nitride layer is deposited by plasma-enhanced chemical vapor deposition.

7. The method according to claim 1, wherein the metal layer has a thickness of less than about 1000 angstroms.

8. An electron microscopy image sample comprising:
   a substrate;
   a metal layer disposed on top of the substrate; and
   a passivation layer comprising silicon and nitrogen and disposed over the entire metal layer, said passivation layer being an uppermost layer,
   wherein the substrate and the metal and passivation layers are sliced to produce a cross-section.

9. The sample according to claim 8, wherein the cross-section of the metal and passivation layers is exposed for imaging by electron microscopy.

10. The sample according to claim 9, wherein the passivation layer is in intimate contact with the metal layer.

11. The sample according to claim 10, wherein the cross-section that is exposed for imaging has a metal layer extending entirely across the width thereof.

12. The sample according to claim 8, wherein a depth of the metal layer in an imaging direction is about 50–100 angstroms.

13. The sample according to claim 12, wherein the substrate includes a silicon base and an insulator layer disposed on top of the silicon base.

14. The sample according to claim 13, wherein part of the metal layer extends through the insulator layer to contact the silicon base.

15. The sample according to claim 14, wherein the substrate includes at least one semiconductor device having active regions and the metal layer contacts one of the active regions of the semiconductor device.

16. The sample according to claim 8, wherein the passivation layer comprises a silicon nitride layer.

17. The sample according to claim 16, wherein the metal layer has a thickness of less than about 1000 angstroms.

* * * * *